United States Patent [19]
Thal

[11] Patent Number: 6,156,039
[45] Date of Patent: Dec. 5, 2000

[54] SNAGGING KNOTLESS SUTURE ANCHOR ASSEMBLY

[76] Inventor: Raymond Thal, 11321 Bright Pond La., Reston, Va. 22094

[21] Appl. No.: 09/369,273

[22] Filed: Aug. 6, 1999

[51] Int. Cl.[7] .................................................. A61B 17/56
[52] U.S. Cl. ............................................................. 606/72
[58] Field of Search .................. 606/72, 73, 74, 606/75, 232, 220

[56] References Cited

U.S. PATENT DOCUMENTS

| | | |
|---|---|---|
| 4,007,743 | 2/1977 | Blake . |
| 4,532,926 | 8/1985 | O'Holla . |
| 4,632,101 | 12/1986 | Freedland . |
| 4,721,103 | 1/1988 | Freedland . |
| 4,870,957 | 10/1989 | Goble et al. . |
| 4,898,156 | 2/1990 | Gatturna et al. . |
| 4,946,468 | 8/1990 | Li . |
| 5,013,316 | 5/1991 | Goble et al. . |
| 5,037,422 | 8/1991 | Hayhurst et al. . |
| 5,084,050 | 1/1992 | Draenert . |
| 5,102,421 | 4/1992 | Anspach, Jr. . |
| 5,141,520 | 8/1992 | Goble et al. . |
| 5,192,303 | 3/1993 | Gatturna et al. . |
| 5,207,679 | 5/1993 | Li . |
| 5,224,946 | 7/1993 | Hayhurst et al. . |
| 5,236,445 | 8/1993 | Hayhurst et al. . |
| 5,370,662 | 12/1994 | Stone et al. . |
| 5,472,452 | 12/1995 | Trott ........................................... 606/72 |
| 5,569,306 | 10/1996 | Thal . |
| 5,658,313 | 8/1997 | Thal . |
| 5,665,112 | 9/1997 | Thal . |
| 5,683,419 | 11/1997 | Thal . |
| 5,709,708 | 1/1998 | Thal . |
| 5,720,765 | 2/1998 | Thal . |
| 5,728,136 | 3/1998 | Thal . |
| 5,782,864 | 7/1998 | Lizardi ....................................... 606/72 |
| 5,891,168 | 4/1999 | Thal ......................................... 606/232 |
| 5,911,721 | 6/1999 | Nicholson et al. ......................... 606/73 |
| 5,957,953 | 9/1999 | Dipoto et al. ............................. 606/232 |
| 5,961,538 | 10/1999 | Pedlick et al. ............................ 606/232 |

*Primary Examiner*—John J. Wilson
*Assistant Examiner*—Eduardo C. Robert
*Attorney, Agent, or Firm*—Hoffman, Wasson & Gitler

[57] ABSTRACT

A snagging knotless suture anchor assembly for attachment of tissue to bone mass. The anchor assembly includes one or more suture elements attached to the anchor. The one or more suture elements are captured by a snag means or recess located on the anchor means. Once the one or more suture elements are captured, the anchor is inserted securely into the bone mass which facilitates a repair of torn away soft tissue.

11 Claims, 5 Drawing Sheets

SNAGGING KNOTLESS SUTURE ANCHOR ASSEMBLY

BACKGROUND OF THE INVENTION

1. Field of the Invention

The present invention relates to a process and device or assembly for use in tissue repair. More particularly, there is provided an enhanced assembly that enables the attachment together or repair of portions of biological tissue, such as tendons or ligaments, to a bone surface. Such device or assembly is used in an unique way with novel components to reattach or attach tissue to bone.

2. Description of the Background Art

Soft tissues, such as tendons and ligaments, generally are attached to bone by small collagenous fibers. These connections are strong but permit the tendons and ligaments to be flexible. When a tissue, or a portion of a tissue, is torn away from the bone and requires repair, a surgeon is often required to repair the detached soft tissue with sutures which are passed through bone tunnels and tied. A number of devices have been developed for securing a ligament or tendon to a bone mass. These devices can be used in place of bone tunneling techniques. These attachment devices are usually inserted through extensive surgical incisions and, in some circumstances, by arthroscopic surgical techniques. The use of bone tunnels for repair can be difficult and generally require large open incisions. Recently, through the advent of endoscopic surgery, where the surgeon looks into a joint cavity with a telescope, there has been a trend to repair soft tissues back to bone through small incisions called portals. The unique free loop knotless suture anchor assemblies described herein facilitate this difficult and precise procedure.

A variety of devices are available for attaching objects to bone, such as screws, staples, cement, suture anchors, and sutures alone. These devices have been used to attach soft tissue, such as ligaments, tendons, muscles, as well as objects such as prostheses, to bone. A suture anchor assembly is a device which utilizes small anchors with suture materials attached thereto. A device, such as a screw, is inserted into the bone mass and anchored in place. After insertion of the anchor, the attached suture is passed through the tissue to be repaired. The tying of a knot in the suture is then required to secure the tissue to the bone. The process of passing the anchored suture through the soft tissue and tying a knot is time consuming and difficult to undertake in the tight space encountered during endoscopic surgery and sometimes even in conventional open surgery.

One example of a suture anchor assembly is disclosed in U.S. Pat. No. 5,370,662, wherein an anchor assembly includes a pre-threaded suture positioned at its posterior. First the anchor is inserted into the bone mass. The attached suture is then passed through the tissue for reattachment. The surgeon is required to tie a knot with the suture to complete the surgical process. Some suture anchors can be passed through the soft tissue first and then into the bone. Most suture anchors need to be inserted into the bone first. Only after this has been accomplished can the sutures be passed through the soft tissue. Alternatives to this procedure include non-suture soft tissue anchor systems. A few of these systems, such as those disclosed in U.S. Pat. Nos. 5,013,316 and 4,532,926, can be used arthroscopically but fixation with these devices may not be as secure as that achieved with sutures. Only a few points of fixation are possible with the non-suture type anchor since the device is relatively large. Therefore suture devices are more favorable. This type of non-suture staple device is disadvantageous in that it has been known to crack the bone during deployment, or accidentally transect the object being attached to the bone. In addition, the device itself has been known to crack or break during or after deployment.

U.S. Pat. Nos. 5,037,422; 5,224,946; and 5,236,445 all disclose bone anchor configurations for attaching sutures within openings formed in bones during joint reconstructive surgery and endoscopic surgical procedures. With all these intricate procedures, the suture itself must be inserted through a tissue mass and tied with a surgical knot to repair the soft tissue to bone.

The applicant has developed a number of mechanisms for a tissue to bone repair which are disclosed in U.S. Pat. Nos. 5,569,306; 5,683,419; 5,728,136; 5,665,112; 5,658,313; 5,720,765; and 5,709,708.

It is an object of the present invention to provide a knotless suture anchor assembly which is easy to use and install.

Another object of the present invention is to provide a snagging knotless suture anchor assembly which allows for secure attachment of soft tissue to a bone mass without the use or requirement of tying a knot during the surgical procedure.

Still another object of the present invention is to provide a snagging knotless suture anchor assembly which is compact and allows a surgeon to easily guide the anchor means into a bone mass or an anchor sleeve in the bone mass, to enhance the security of the repair.

Yet another object of the present invention is to provide a process whereby a plurality of snagging knotless suture anchor assemblies can be used to effectively attach or reattach tissue to bone.

A primary feature of the present invention is to provide snagging knotless anchor assembly that includes an unique snag-type or capture means on an anchor means which facilitates engagement of the anchor means with one or more suture elements which are attached to the anchor means, for drawing soft tissue to the bone mass. The one or more suture elements having one more snagger stop elements thereon, which engage the capture means of the anchor.

SUMMARY OF THE INVENTION

In accordance with the above objects, the present invention is directed to an assembly and a process of using at least one snagging knotless suture anchor assembly for attachment or reattachment of biological soft tissue to bone. The unique snagging knotless suture anchor assembly may include a hollow anchoring sleeve which can be installed into a bone mass for receiving the anchor therein. The hollow anchoring sleeve, or anchor means itself, can have varying shaped or surfaced exteriors for secure capturing or engagement with a bone mass. Each anchor means engages one or more suture elements, which has one end attached to the anchor anchoring sleeve, at a second location or end of the element(s) near to a snagger step element.

Incorporated by reference are U.S. Pat. Nos. 4,007,743; 4,632,101; 4,721,103; 4,870,957; 4,898,156; 4,946,468; 5,084,050; 5,102,421; 5,141,520; 5,192,303; and 5,207,679, which all illustrate varying structures which may embody the anchor means or the exterior of the anchoring sleeve of the invention.

Further, if desired, the hollow anchoring sleeve can contain a collar on its rear section or rear side to control the depth of sleeve insertion into the bone and prevent excessive insertion depth. The anchor means of the assembly has a configuration which allows for secure capturing of the hollow anchoring sleeve, when used, and a snag or recess component for securing the one or more suture elements. A first end of the anchor can be pointed, U-shaped or frusto-conical in shape. The anchor's overall exterior can be ribbed, beaded, threaded, or expandable or can contain one or more protruding prongs for secure mating with the bone or anchoring sleeve.

The anchor means has located thereon or therein an unique snag means in the shape of a hook, or other type projection, or a U-shaped recess cut into the anchor means, or a slit cut into an existing opening in the anchor, for engaging the snagger stop element of the one or more suture element(s) which are attached to the anchor means. One particular embodiment provides a U-shaped recess at the apex of the anchor whereby one or more snagger stop element(s) are snagged or captured by the anchor.

The one or more suture elements can be a single continuous configuration or a plurality of suture lengths tied or attached together by any suitable means. The suture element is attached to the anchor means at any desired location thereon by any desired mechanism. A hook portion or projection on the anchor means can be made of the same material as the entire anchor means or a different material, as desired. The anchor assembly can be inserted during an open procedure, or an endoscopic procedure. In a preferred method, the one or more suture elements are passed through or maneuvered around the soft tissue. Next, the anchor means is pressed into the bone mass by passing same through the tissue or around the tissue. The suture one or more elements are then captured by the snag means of the anchor. The anchor means engages the snagger stop element and is then inserted into the bone mass or a hollowing anchoring sleeve which has been inserted into the bone mass.

If desired, an user can use a plurality of assemblies to effectuate a broader repair.

The incisions, cuts or passages in the tissue can be accomplished by using needle and suture loop attachment assemblies which have been added to the one or more suture elements. Upon capture of the snagger stop elements of the one or more suture elements the needle and suture loop attachment assembly is cut away and discarded. This assembly facilitates the method of stitching and reattachment.

Numerous other features of various embodiments of the enhanced sleeve and loop knotless suture anchor assembly will be apparent from the following detailed description and the accompanying drawings.

DETAILED DESCRIPTION OF THE PRESENT INVENTION

Figure 1:
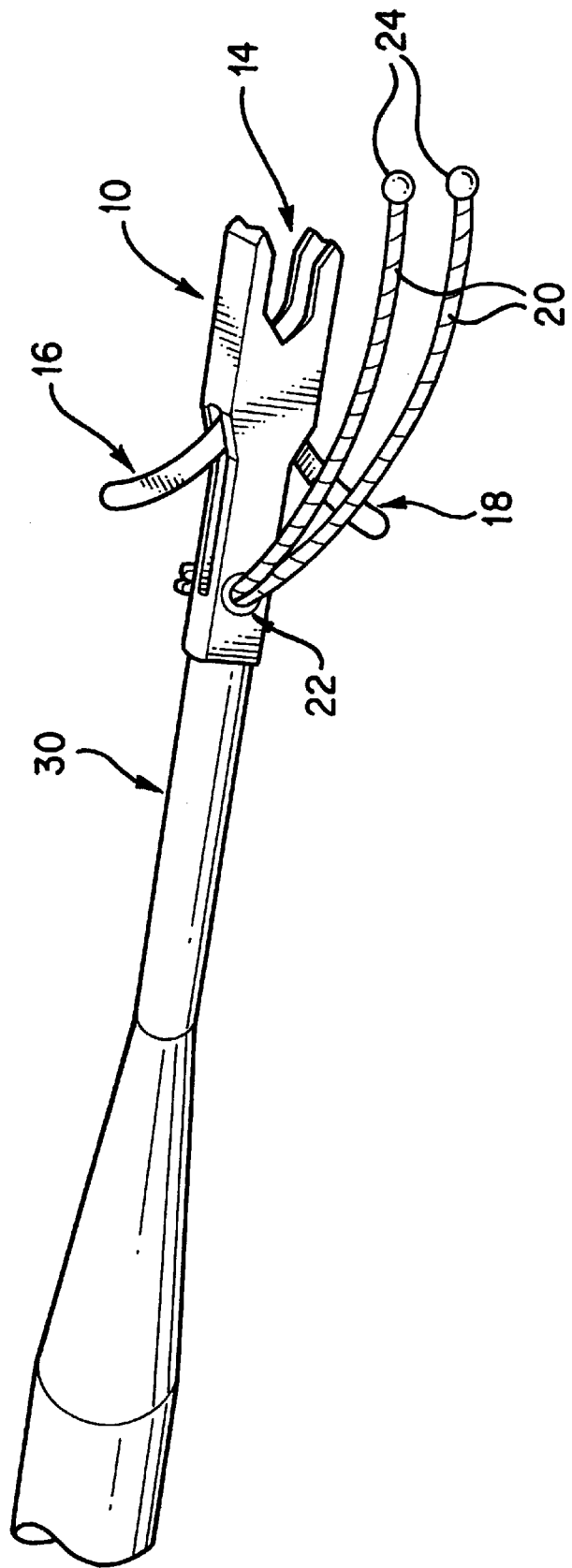
FIG. 1 is a perspective view of snagging knotless suture anchor assembly having a depression or U-shaped snag recess.
Figure 2:
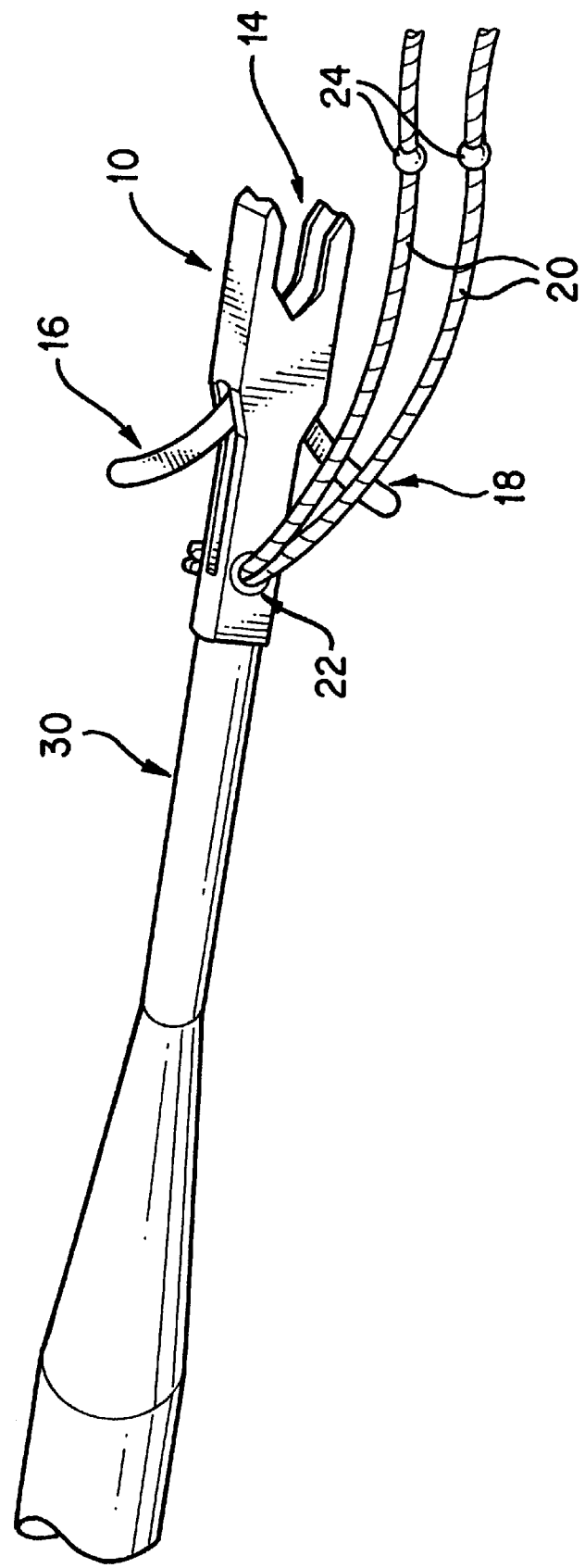
FIG. 2 is a perspective view of an alternate embodiment of a snagging knotless suture anchor assembly having a depression or U-shaped snag recess.
Figure 3:
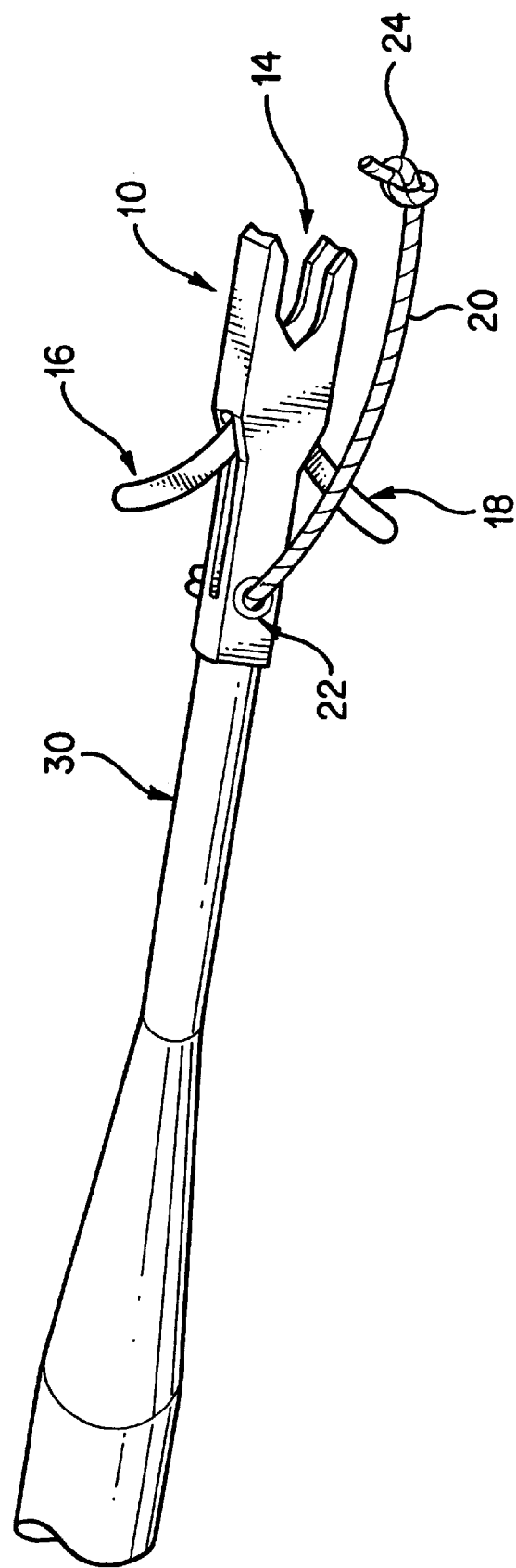
FIG. 3 is a perspective view of an alternate embodiment of a snagging knotless suture anchor assembly having a depression or U-shaped snag recess.

Referring to FIGS. 1, 2 and 3, there is depicted preferred embodiments of the snagging knotless suture anchor assembly. More particularly, FIG. 1 illustrates an anchor means 10 having prongs 16 and 18 which facilitate the attachment of the anchor means 10 to a bone mass. Provided in the body of the anchor means is a snag recess 14 for capturing one or more suture elements. The device can also contain, or be configured, with umbrella spokes or any other type of engaging features on its exterior for securing an attachment with a bone mass. All of these exterior attachment features are known to the industry and incorporated herein by reference.

The anchor means 10 has attached thereto one or more suture elements 20 as designated in the figure. The suture elements 20 are attached to the anchors means 10 at any desirable location and by any suitable means. FIG. 1 depicts a slot 22 for receiving the elements. Along the length of the suture element(s) 20, is one or more snagger stop elements 24 which can take any suitable shape and can be located as desired along the length of the suture element 20.

Also depicted in FIG. 1 is a removable applicator device 30 which engages the anchor means 10 and allows a user to insert the anchor means into bone.

FIG. 2 illustrates an alternate embodiment of the anchor means. Depicted is a snagging knotless suture anchor assembly having an anchor means 10, and a snag recess 14. This embodiment illustrates one or more suture elements 20, having at least one snagger stop means 24 located along the length of the elements 20. The snagger stop means 24 can be permanently affixed to the suture elements 20, or they can be moveable and lock at a desired position to facilitate a desired length of the elements 20 to be snagged by the recess 14 during a repair.

FIG. 3 depicts an alternate embodiment of the anchor means 10. Depicted is an anchor means 10 and a snag recess 14. This embodiment illustrates one suture element 20, having at least one snagger stop means, a knot 24, affixed to the suture element 20. The knot 24 is captured in the recess 14 during a tissue repair.

Figure 4:
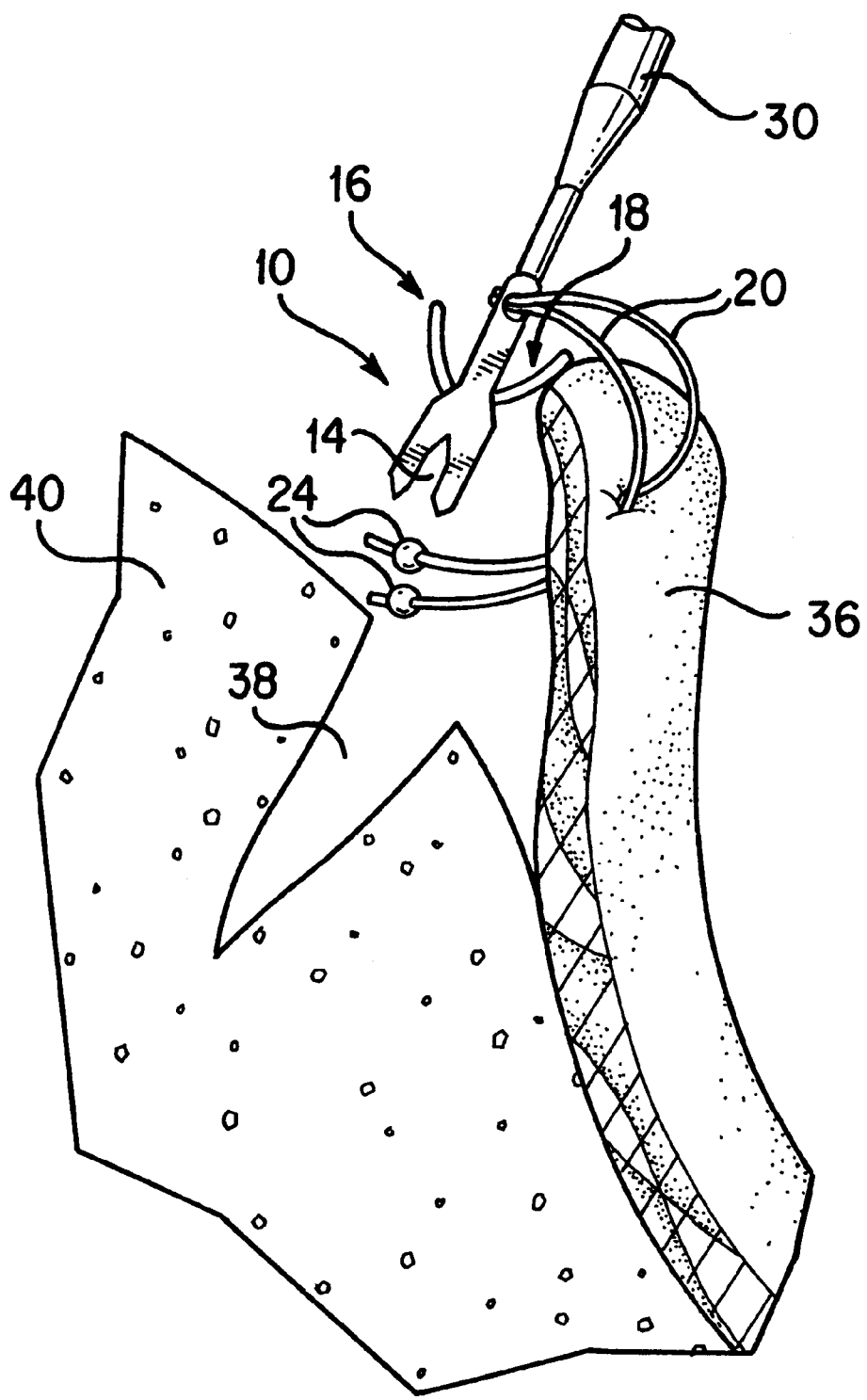
FIG. 4 is a depiction of a process of performing a tissue repair using the snagging knotless suture anchor assembly of the present invention.

FIG. 4 illustrates one preferred methodology of a repair utilizing the snagging knotless suture anchor assembly of the present invention.

The one or more suture elements are pulled through tissue 36 to align same with a recess 38 in a bone mass 40. The recess can be predrilled or formed during insertion or depression of anchor means 10 into the bone mass 40.

The anchor means 10 is then pressed, using an applicator device 10 snagging the one or more suture elements 20 in its recess 14 and forcing them into the recess 38 of the bone mass 40. The one or more snagger stop means 24 are held firmly against the recess 14 when the anchor means 10 is placed into the bone mass 40.

Figure 5:
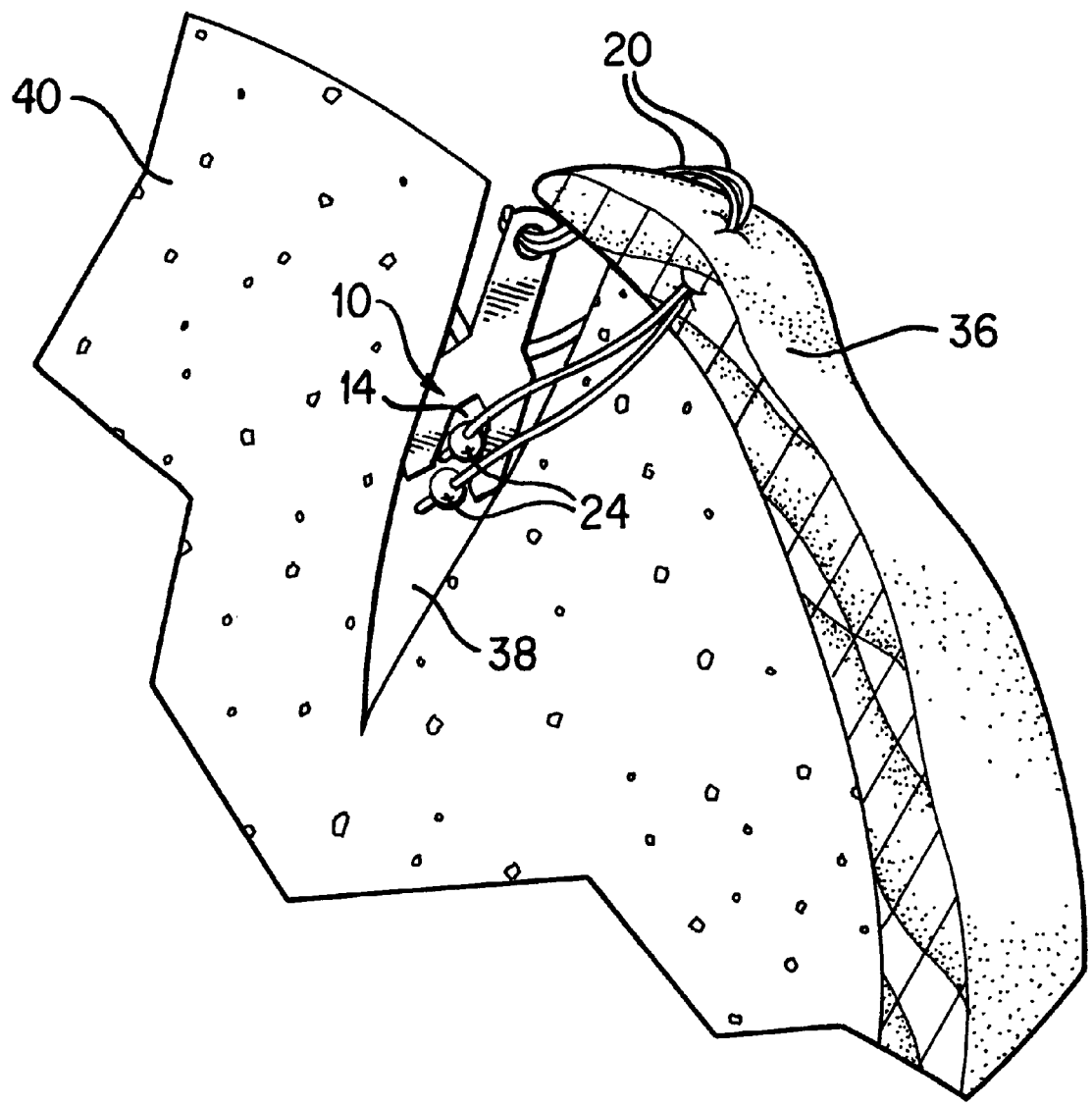
FIG. 5 is a depiction of a completed tissue repair.

FIG. 5 illustrates a complete repair of tissue 36 to bone mass 40. The anchor means 10 has been inserted into the recess 38 of the bone mass 40. The one or more suture elements 20 are snagged by the recess 14 and held in securely by the one or more snagger stopping means 24.

The one or more suture elements can be made of various materials, or they can be molded as part of an entire anchor assembly. The suture can be permanently affixed to the anchor means or they can be slidably attached to the anchor means.

The one or more snagger stopper means 24 depicted in the figures can be thickenings on the suture elements, beads, knots, enlargements or made of anything suitable to allow for capture in the anchor means recess 14.

In situations throughout the discussion above, the terminology "secure attachment of tissue to bone mass" has been used. Such terminology refers to the attachment or reattachment of tissue to a bone mass by securely binding the tissue to the bone mass utilizing the novel snagging knotless suture anchor assembly. The suture element can be made up of a known suture material, or it can be made of polymer materials, or can be formed of bioabsorbable material such as a polylactide polymer.

While a preferred embodiment of the invention is illustrated, it should be understood that the present disclosure is made by way of example and that variations to the structure shown and its use are possible within the scope of this disclosure without departing from the subject matter coming within the scope of the claims.

What is claimed is:

1. A snagging knotless suture anchor assembly for attachment of tissue to a bone mass, the assembly comprising an anchor means having a first end and a second end, a snag means located at the first end of the anchor means, and one or more suture elements attached to the second end of the anchor means, the one or more suture elements having a first end and a second end, wherein the first end is attached to the second end of the anchor means and the one or more suture elements has one or more snagger stop elements attached thereon, whereby the snag means captures the one or more snagger stop elements during a procedure to draw the tissue into secure attachment with a bone mass.

2. The snagging knotless suture anchor assembly as claimed in claim 1, wherein the snag means is a recess formed in the anchor means or an element attached to the anchor means to capture the one or more snagger stop elements allowing the tissue to be drawn to the bone mass.

3. The snagging knotless suture anchor assembly as claimed in claim 1, further comprising a hollow anchoring sleeve to engage and secure the anchor means for installation and attachment to the bone mass.

4. The snagging knotless suture anchor assembly as claimed in claim 3, wherein the hollow anchoring sleeve has a collar at a top section facilitating its attachment to said bone mass.

5. The method for the attachment of tissue to a bone mass utilizing the snagging knotless suture anchor assembly as claimed in claim 3, comprising the steps of:
   a) installing the hollow anchoring sleeve into the bone mass;
   b) passing the one or more suture elements through the tissue; and
   c) capturing the one or more snagger stop elements with the snag means of said anchor means; and installing the anchor means into the hollow anchoring sleeve.

6. The snagging knotless suture anchor assembly as claimed in claim 1, wherein an exterior surface of the anchor means has prongs, screws or umbrella spokes for installation and attachment to said bone mass.

7. The snagging knotless suture anchor assembly as claimed in claim 1, wherein the one or more snagger stop elements are located at an end of the one or more suture elements.

8. The snagging knotless suture anchor assembly as claimed in claim 1, wherein the one or more snagger stop elements are: thickenings on the one or more suture elements, beads, knots or suture enlargements.

9. The snagging knotless suture anchor assembly as claimed in claim 1, wherein the one or more suture elements are made of suture thread or are molded.

10. The snagging knotless suture anchor assembly as claimed in claim 1, wherein the one or more suture elements are slidably attached, fixed or molded to the anchor means.

11. A method for the attachment of tissue to a bone mass utilizing the snagging knotless suture anchor assembly as claimed in claim 1, comprising the steps of:
   a) passing the one or more suture elements through the tissue; and
   b) capturing the one or more snagger stop elements with the snag means of the anchor means; and installing the anchor means into the bone mass for attachment of the tissue to the bone mass.

* * * * *